United States Patent
Hagiya

(10) Patent No.: US 7,956,223 B2
(45) Date of Patent: Jun. 7, 2011

(54) METHOD FOR PRODUCING HALOGEN-SUBSTITUTED BENZENEDIMETHANOL

(75) Inventor: Koji Hagiya, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 208 days.

(21) Appl. No.: 12/160,317

(22) PCT Filed: Jan. 16, 2007

(86) PCT No.: PCT/JP2007/050869
§ 371 (c)(1), (2), (4) Date: Jul. 9, 2008

(87) PCT Pub. No.: WO2007/086330
PCT Pub. Date: Aug. 2, 2007

(65) Prior Publication Data
US 2010/0222613 A1 Sep. 2, 2010

(30) Foreign Application Priority Data
Jan. 24, 2006 (JP) .................. 2006-014720

(51) Int. Cl.
C07C 29/147 (2006.01)
(52) U.S. Cl. ....................... 568/814; 568/811
(58) Field of Classification Search .......... None
See application file for complete search history.

(56) References Cited

U.S. PATENT DOCUMENTS

| 4,927,852 A | 5/1990 | Robson et al. |
| 5,583,131 A | 12/1996 | Bridger et al. |
| 6,759,558 B2 | 7/2004 | Rodefeld |
| 7,678,947 B2 * | 3/2010 | Hagiya .......... 568/811 |
| 2002/0156330 A1 | 10/2002 | Rodefeld |

FOREIGN PATENT DOCUMENTS

| EP | 1 247 792 A2 | 10/2002 |
| JP | 11-43455 A | 2/1999 |
| JP | 2002-332251 A | 11/2002 |

OTHER PUBLICATIONS

Database CAPLUS on STN, Acc. No. 2006:49483, Wang et al., CN 1631868 (Jun. 29, 2005) (abstract).*
A. Mishra et al., Dyes and Pigments, (2004), vol. 63, issue 2, pp. 191-202.

* cited by examiner

*Primary Examiner* — Brian J Davis
(74) *Attorney, Agent, or Firm* — Sughrue Mion, PLLC

(57) ABSTRACT

A method for producing a halogen-substituted benzenedimethanol represented by the formula (2):

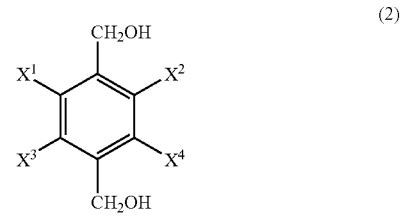

wherein $X^1$, $X^2$, $X^3$ and $X^4$ are the same or different and each independently represent a hydrogen atom or a halogen atom, provided that $X^1$, $X^2$, $X^3$ and $X^4$ are not hydrogen atoms at the same time,
by reacting a halogen-substituted terephthalic acid represented by the formula (1):

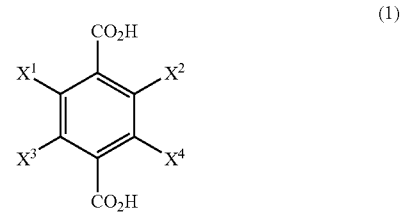

wherein $X^1$, $X^2$, $X^3$ and $X^4$ are the same meanings as defined above,
with a borohydride compound in an organic solvent, followed by contacting the obtained reaction mixture with hydrogen chloride at 40 to 70° C.

9 Claims, No Drawings

METHOD FOR PRODUCING HALOGEN-SUBSTITUTED BENZENEDIMETHANOL

TECHNICAL FIELD

The present invention relates to a method for producing a halogen-substituted benzenedimethanol.

BACKGROUND ART

A halogen-substituted benzenedimethanol is an important compound as raw materials and intermediates of pharmaceuticals and agrichemicals, and especially, U.S. Pat. No. 4,927,852 discloses 2,3,5,6-tetrafluorobenzenedimethanol is useful as an intermediate of household pesticides.

As a method for producing the halogen-substituted benzenedimethanol, U.S. Pat. No. 6,759,558 discloses a method comprising reacting 2,3,5,6-tetrafluoroterephthalic acid with sodium borohydride followed by reacting with an alkylating agent, sulfuric acid, an alkyl sulfonic acid or an aryl sulfonic acid.

DISCLOSURE OF THE INVENTION

The present invention provides a method for producing a halogen-substituted benzenedimethanol represented by the formula (2):

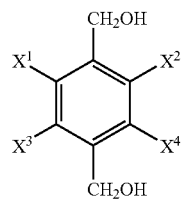

(2)

wherein $X^1$, $X^2$, $X^3$ and $X^4$ are the same or different and each independently represent a hydrogen atom or a halogen atom, provided that $X^1$, $X^2$, $X^3$ and $X^4$ are not hydrogen atoms at the same time,
by reacting a halogen-substituted terephthalic acid represented by the formula (1):

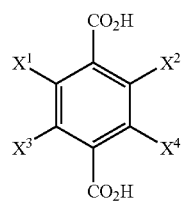

(1)

wherein $X^1$, $X^2$, $X^3$ and $X^4$ are the same meanings as defined above,
with a borohydride compound in an organic solvent, followed by contacting the obtained reaction mixture with hydrogen chloride at 40 to 70° C.

BEST MODE FOR CARRYING OUT THE PRESENT INVENTION

In the halogen-substituted terephthalic acid represented by the formula (1), examples of the halogen atom represented by $X^1$, $X^2$, $X^3$ and $X^4$ include a fluorine atom, a chlorine atom and a bromine atom. $X^1$, $X^2$, $X^3$ and $X^4$ are preferably fluorine atoms.

Examples of the halogen-substituted terephthalic acid represented by the formula (1) include 2-fluoroterephthalic acid, 2-chloroterephthalic acid, 2,5-difluoroterephthalic acid, 2,6-difluoroterephthalic acid, 2,3-difluoroterephthalic acid, 2,5-dichloroterephthalic acid, 2,6-dichloroterephthalic acid, 2,3-dichloroterephthalic acid, 2,3,5-trifluoroterephthalic acid, 2,3,5-trichloroterephthalic acid, 2,3,5,6-tetrafluoroterephthalic acid, 2,3,5,6-tetrachloroterephthalic acid and 2,3,5-trifluoro-6-chloroterephthalic acid.

The halogen-substituted terephthalic acid represented by the formula (1) can be produced, for example, according to a known method such as a method comprising hydrolyzing the corresponding halogen-substituted terephthalonitrile (e.g. U.S. Pat. No. 5,792,887).

Examples of the borohydride compound include an alkali metal borohydride such as sodium borohydride, lithium borohydride and potassium borohydride; and an alkaline earth metal borohydride such as calcium borohydride and magnesium borohydride. In the view of availability, the alkali metal borohydride is preferable and sodium borohydride is more preferable.

While a commercially available borohydride compound is usually used, those prepared according to a known method may be used. For example, sodium borohydride can be prepared easily from a boric acid ester and sodium hydride. Alternatively, other borohydride compounds can be prepared by a reaction of sodium borohydride and the corresponding metal halide, and for example, calcium borohydride is obtained by a reaction of sodium borohydride and calcium chloride. When the borohydride compound is prepared to use, those previously prepared may be added to the reaction system and it may be prepared in the reaction system.

The used amount of the borohydride compound is usually 1 mole or more per 1 mole of the halogen-substituted terephthalic acid represented by the formula (1). While there is no specific upper limit, in the viewpoint of economic efficiency, it is practically 5 moles or less and preferably 2 to 3 moles of less.

Examples of the organic solvent include ether solvents such as diethyl ether, methyl tert-butyl ether, tetrahydrofuran, dioxane, diisopropyl ether and dimethoxyethane, and aromatic hydrocarbon solvents such as toluene, xylene and chlorobenzene, and ether solvents are preferable, and dimethoxyethane is more preferable. While the used amount of the organic solvent is not particularly limited, it is usually 1 to 100 parts by weight per 1 part by weight of the halogen-substituted terephthalic acid represented by the formula (1).

The reaction temperature is usually −20 to 200° C., and preferably 0 to 100° C.

The reaction of the halogen-substituted terephthalic acid represented by the formula (1) and the borohydride compound is conducted by mixing the organic solvent, the halogen-substituted terephthalic acid represented by the formula (1) and the borohydride compound. The mixing order is not particularly limited, and examples thereof include a method comprising adding the halogen-substituted terephthalic acid represented by the formula (1) or a mixture of the halogen-substituted terephthalic acid represented by the formula (1) and the organic solvent into a mixture of the organic solvent and the borohydride compound.

The reaction time is usually 0.5 to 24 hours.

While the reaction is usually carried out at normal pressure, it may be carried out under pressure. The progress of the reaction can be checked by a conventional analytical means such as gas chromatography and high performance liquid chromatography.

The desired halogen-substituted benzenedimethanol represented by the formula (2) can be obtained by contacting the reaction mixture obtained in the reaction of the halogen-substituted terephthalic acid represented by the formula (1) and the borohydride compound with hydrogen chloride at 40 to 70° C.

As hydrogen chloride, hydrogen chloride gas, hydrochloric acid and an organic solvent solution of hydrogen chloride can be used, and in the viewpoint of operability and availability, hydrochloric acid is preferable. A commercially available hydrochloric acid may be used as it is and may be mixed with an inert gas on the reaction, an organic solvent, water or the like to use. When hydrochloric acid is used, one having high concentration of hydrogen chloride is preferably used and concentrated hydrochloric acid is more preferable. Examples of the organic solvent solution of hydrogen chloride include hydrogen chloride/dioxane solution, hydrogen chloride/tetrahydrofuran solution and hydrogen chloride/dimethoxyethane solution.

The used amount of hydrogen chloride is usually 1 mole or more per 1 mole of the borohydride compound used in the above-mentioned reaction of the halogen-substituted terephthalic acid represented by the formula (1) and the borohydride compound. While there is no upper limit particularly, it is practically 10 moles or less in view of economic aspect and volume efficiency.

The contact of the reaction mixture obtained in the above-mentioned reaction of the halogen-substituted terephthalic acid represented by the formula (1) and the borohydride compound with hydrogen chloride is conducted, for example, by a method comprising adding hydrogen chloride into the reaction mixture adjusted at 40 to 70° C. The reaction mixture may be used as it is and after adding the above-mentioned ether solvent and the above-mentioned aromatic hydrocarbon solvent thereto.

The contact time of the reaction mixture and hydrogen chloride is usually 0.5 to 24 hours.

While the contact of the reaction mixture and hydrogen chloride is carried out at normal pressure, it may be carried out under pressure. The progress of the reaction can be checked by a conventional analytical means such as gas chromatography and high performance liquid chromatography.

After completion of the reaction, the halogen-substituted benzenedimethanol represented by the formula (2) can be isolated by, if necessary adding water or a water-insoluble solvent, conducting extraction and concentrating the obtained organic layer. The isolated halogen-substituted benzenedimethanol represented by the formula (2) may be further purified by a conventional purification means such as recrystallization and column chromatography.

Examples of thus obtained halogen-substituted benzenedimethanol represented by the formula (2) include 2-fluoro-1,4-benzendimethanol, 2-chloro-1,4-benzendimethanol, 2,5-difluoro-1,4-benzendimethanol, 2,6-difluoro-1,4-benzendimethanol, 2,3-difluoro-1,4-benzendimethanol, 2,5-dichloro-1,4-benzendimethanol, 2,6-dichloro-1,4-benzendimethanol, 2,3-dichloro-1,4-benzendimethanol, 2,3,5-trifluoro-1,4-benzendimethanol, 2,3,5-trichloro-1,4-benzendimethanol, 2,3,5,6-tetrafluorobenzendimethanol, 2,3,5,6-tetrachlorobenzendimethanol and 2,3,5-trifluoro-6-chlorobenzendimethanol.

EXAMPLES

The present invention will be illustrated in more detail by Examples below. The present invention is not limited to these Examples. The analysis was conducted by high performance liquid chromatography absolute calibration method.

Example 1

Into a 200 ml flask, 2.58 g of sodium borohydride and 25 g of dimethoxyethane were charged at room temperature and the obtained mixture was heated to 50° C. A mixed solution of 6.1 g of 2,3,5,6-tetrafluoroterephthalic acid and 20 g of dimethoxyethane was added dropwise to the mixture over 1 hour while stirring at the same temperature to effect the reaction for 7 hours at 60° C. After adding 20 g of toluene to the reaction mixture and cooling the obtained mixture at 50° C., 8.5 g of 35% by weight aqueous hydrochloric acid was added thereto dropwise over 1 hour and the resultant mixture was stirred and kept for 6 hours at 60° C. To the obtained mixture, 30 g of water was added. After leaving the mixture at rest, the mixture was separated to an organic layer and an aqueous layer. The aqueous layer was extracted twice with 30 g of ethyl acetate and the obtained oil layers were mixed with the organic layer previously obtained. The organic layer after mixing was washed with 10 g of a saturated potassium carbonate and then 10 g of water, and the organic layer was concentrated to obtain the solid. The solid was recrystallized with toluene and hexane to obtain 5.35 g of a white powder solid containing 2,3,5,6-tetrafluorobenzenedimethanol. The purity of 2,3,5,6-tetrafluorobenzenedimethanol was 95.1% and the yield thereof was 95%.

Example 2

Into a 200 ml flask, 2.3 g of sodium borohydride and 25 g of dimethoxyethane were charged at room temperature and the obtained mixture was heated to 50° C. A mixed solution of 6.1 g of 2,3,5,6-tetrafluoroterephthalic acid and 30 g of dimethoxyethane was added dropwise to the mixture over 1 hour while stirring at the same temperature to effect the reaction for 2 hours at 60° C. To the reaction mixture, 15.5 g of 14% by weight hydrogen chloride/dioxane solution was added dropwise over 3 hours, and then the resultant mixture was stirred and kept at the same temperature for 5 hours. After cooling the obtained mixture at 25° C., 30 g of 5% by weight hydrochloric acid was added thereto and the mixture was separated to an organic layer and an aqueous layer. The aqueous layer was extracted twice with 30 g of toluene and the obtained oil layers were mixed with the organic layer previously obtained. The organic layer after mixing was washed with 10 g of water, and the organic layer was concentrated to obtain the solid. The solid was recrystallized with toluene and hexane to obtain 5.6 g of a white powder solid containing 2,3,5,6-tetrafluorobenzenedimethanol. The purity of 2,3,5,6-tetrafluorobenzenedimethanol was 87.0% and the yield thereof was 90%.

Comparative Example 1

Into a 200 ml flask, 2.58 g of sodium borohydride and 25 g of dimethoxyethane were charged at room temperature and the obtained mixture was heated to 50° C. A mixed solution of 6.1 g of 2,3,5,6-tetrafluoroterephthalic acid and 20 g of dimethoxyethane was added dropwise to the mixture over 1 hour while stirring at the same temperature to effect the reaction for 7 hours at 60° C. After adding 25 g of toluene to the reaction mixture and cooling the obtained mixture at 25° C., 8.5 g of 35% by weight aqueous hydrochloric acid was added thereto dropwise over 1 hour at 25 to 30° C. and the resultant mixture was stirred and kept for 6 hours at 25 to 30°

C. To the obtained mixture, 30 g of water was added. After leaving the mixture at rest, the mixture was separated to an organic layer and an aqueous layer. The aqueous layer was extracted twice with 30 g of ethyl acetate and the obtained oil layers were mixed with the organic layer previously obtained. The organic layer after mixing was washed with 10 g of a saturated potassium carbonate and then 10 g of water, and the organic layer was concentrated to obtain the solid containing 2,3,5,6-tetrafluorobenzenedimethanol. The yield of 2,3,5,6-tetrafluorobenzenedimethanol was 33%. Alternatively, 4-carboxy-2,3,5,6-tetrafluorobenzyl alcohol was formed as by-products in the yield of 29%, and a raw material 2,3,5,6-tetrafluoroterephthalic acid remained in 38%.

INDUSTRIAL APPLICABILITY

According to the present invention, a halogen-substituted benzenedimethanol which is important as intermediates of pharmaceuticals and agrichemicals or the like, can be produced in a good yield, and therefore, it is useful industrially.

The invention claimed is:

1. A method for producing a halogen-substituted benzenedimethanol represented by the formula (2):

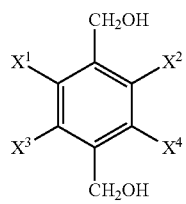

(2)

wherein $X^1$, $X^2$, $X^3$ and $X^4$ are the same or different and each independently represent a hydrogen atom or a halogen atom, provided that $X^1$, $X^2$, $X^3$ and $X^4$ are not hydrogen atoms at the same time,
by reacting a halogen-substituted terephthalic acid represented by the formula (1):

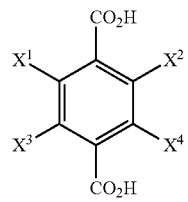

(1)

wherein $X^1$, $X^2$, $X^3$ and $X^4$ are the same meanings as defined above,
with a borohydride compound in an organic solvent, followed by contacting the obtained reaction mixture with hydrogen chloride at 40 to 70° C.

2. The method according to claim 1, wherein $X^1$, $X^2$, $X^3$ and $X^4$ are fluorine atoms.

3. The method according to claim 1 or 2, wherein the borohydride compound is an alkali metal borohydride.

4. The method according to claim 3, wherein the alkali metal borohydride is sodium borohydride.

5. The method according to claim 1 or 2, wherein the organic solvent is an ether solvent.

6. The method according to claim 5, wherein the ether solvent is dimethoxyethane.

7. The method according to claim 1, wherein the used amount of the borohydride compound is 1 to 5 moles per 1 mole of the halogen-substituted terephthalic acid represented by the formula (1).

8. The method according to claim 1, wherein hydrochloric acid is used as hydrogen chloride.

9. The method according to claim 1 or 2, wherein the used amount of hydrogen chloride is 1 to 10 moles per 1 mole of the borohydride compound used in the reaction of the halogen-substituted terephthalic acid represented by the formula (1) and the borohydride compound.

* * * * *